US012605427B2

(12) United States Patent
Bentz et al.

(10) Patent No.: US 12,605,427 B2
(45) **Date of Patent: *Apr. 21, 2026**

(54) SUBLINGUAL SEMAGLUTIDE-BPC 157 COMBINATION FOR WEIGHT LOSS

(71) Applicant: Red Mountain Med Spa, LLC, Scottsdale, AZ (US)

(72) Inventors: Suzanne Bentz, Scottsdale, AZ (US); Austin Lucht, Scottsdale, AZ (US); Shelly Kocher, Scottsdale, AZ (US)

(73) Assignee: RED MOUNTAIN MED SPA, LLC, Scottsdale, AZ (US)

( * ) Notice: Subject to any disclaimer, the term of this patent is extended or adjusted under 35 U.S.C. 154(b) by 511 days.

This patent is subject to a terminal disclaimer.

(21) Appl. No.: 18/317,232

(22) Filed: May 15, 2023

(65) Prior Publication Data

US 2024/0382565 A1 Nov. 21, 2024

(51) Int. Cl.
| | |
|---|---|
| *A61K 38/26* | (2006.01) |
| *A61K 9/00* | (2006.01) |
| *A61K 9/20* | (2006.01) |
| *A61K 38/10* | (2006.01) |

(52) U.S. Cl.
CPC .............. *A61K 38/26* (2013.01); *A61K 9/006* (2013.01); *A61K 9/2009* (2013.01); *A61K 9/2013* (2013.01); *A61K 9/2018* (2013.01); *A61K 9/2027* (2013.01); *A61K 38/10* (2013.01)

(58) Field of Classification Search
CPC ...... A61K 38/26; A61K 9/006; A61K 9/2009; A61K 9/2013; A61K 9/2018; A61K 9/2027; A61K 38/10
See application file for complete search history.

(56) References Cited

U.S. PATENT DOCUMENTS

| | | | | |
|---|---|---|---|---|
| 11,173,124 B2 * | 11/2021 | Pechenov | ............ | A61K 9/4858 |
| 11,833,189 B1 * | 12/2023 | Bentz | ................... | A61K 9/2018 |
| 2024/0041983 A1 * | 2/2024 | Föger | ................... | A61K 9/2013 |

FOREIGN PATENT DOCUMENTS

| | | | | |
|---|---|---|---|---|
| CN | 114031680 A | * | 2/2022 | ........... C07K 14/605 |
| WO | WO-2022049310 A1 | * | 3/2022 | ................ A61P 3/10 |

OTHER PUBLICATIONS

Xue XC, Wu YJ, Gao MT, Li WG, Zhao N, Wang ZL, Bao CJ, Yan Z, Zhang YQ. Protective effects of pentadecapeptide BPC 157 on gastric ulcer in rats. World J Gastroenterol. Apr. 1, 2004;10(7):1032-6. doi: 10.3748/wjg.v10.i7.1032. PMID: 15052688; PMCID: PMC4717094. (Year: 2004).*

Dixit & Puthli (Oral strip technology: Overview and future potential, Journal of Controlled Release, vol. 139, Issue 2, 2009, pp. 94-107, ISSN 0168-3659, https://doi.org/10.1016/j.jconrel.2009.06.014.) (Year: 2009).*

Wang YW, Lin JH, Yang CS. Meta-analysis of the association between new hypoglycemic agents and digestive diseases. Medicine (Baltimore). Aug. 26, 2022;101(34):e30072. doi: 10.1097/MD.0000000000030072. PMID: 36042668; PMCID: PMC9410596. (Year: 2022).*

Tuman P. Rai, Anup Pramanik, Dipayan Purakayastha, Madhvi Ghadge, Shiv Garg. Sublingual Route for the Systemic Delivery of Drugs. World J PharmSci 2019; 7(1): 38-45. (Year: 2019).*

* cited by examiner

Primary Examiner — Lianko G Garyu
Assistant Examiner — Daliyah M. Brown
(74) Attorney, Agent, or Firm — SNELL & WILMER L.L.P.

(57) ABSTRACT

Sublingual Semaglutide compositions may comprise both Semaglutide or a salt thereof and a gastric peptide or salt thereof, in combination. The use of a gastric peptide mitigates gastrointestinal side effects of Semaglutide. A weight loss regimen comprises administration of sublingual Semaglutide compositions in the physical form of sublingual tablets. In preferred embodiments, each sublingual Semaglutide tablet provides about 500 mcg Semaglutide or 750 mcg Semaglutide in combination with 300 mcg of gastric peptide, with the gastric peptide preferably comprising Body Protection Compound-157 (BPC-157). Sublingual administration of Semaglutide finds use in suppressing appetite, losing weight, and maintaining a desired personal appearance.

6 Claims, No Drawings

SUBLINGUAL SEMAGLUTIDE-BPC 157 COMBINATION FOR WEIGHT LOSS

FIELD

This disclosure generally relates to pharmaceutical compositions used for weight loss, and more specifically, to sublingually administered weight loss compositions comprising Semaglutide sodium salt and BPC-157 acetate in combination.

BACKGROUND

Individuals from industrialized countries are often increasingly obsessed by health and beauty. These individuals typically help fuel a multi-billion dollar market for over the counter (OTC) diet products, medically assisted weight loss and anti-aging treatments (e.g., prescription drugs, bariatric surgery, cosmetic surgery, cosmetics, etc.). Some individuals may find difficulty in maintaining and coordinating both a proper diet and an exercise regimen, such that such individuals often turn to pharmaceutically active formulations and programs promoting rapid weight loss and body sculpting.

Semaglutide (an antidiabetic drug sold under the brand name Ozempic®) Novo Nordisk is now being prescribed off-label as an anti-obesity medication for weight loss. This drug was approved as a once-weekly injection at a dose range of 0.1 mg to 1.0 mg for type-2 diabetes (TD2). The once-per-day 7 mg or 14 mg oral Semaglutide tablet (Rybelsus®) was also approved for TD2 and is also seeing off-label use as an anti-obesity medication for weight loss. Further, 2.4 mg/0.75 mL weekly injected Semaglutide sold under the brand name Wegovy® is now approved in the U.S. by the FDA for weight loss. For a discussion of oral administration of peptides including Semaglutide, see D. J. Brayden, et al., "Systemic delivery of peptides by the oral route: Formulation and medicinal chemistry approaches," *Advanced Drug Delivery Reviews*, 157, 2-36, (2020).

The growing trend to use Semaglutide for weight loss only is beginning to cause shortages of Semaglutide for diabetes. However, both subcutaneous (SC) injection and oral administration of Semaglutide cause unwanted side effects. These include, for example, anxiety, darkened urine, headaches, swelling of facial parts, nightmares, abdominal pain, stomach pain, side pain radiating to the back, skin rashes, unusual tiredness and/or unusual weakness. Orally administered 14 mg Semaglutide tablets and 2.4 mg/0.75 mL weekly SC administered Semaglutide injection cause nausea, vomiting, abdominal pain, diarrhea, constipation, indigestion, fatigue and headaches.

As such, there is an unmet need for new Semaglutide formulations administrable in ways not previously considered for weight loss and weight management, particularly so that individuals desirous of long-term weight loss can stay on their weight loss program.

SUMMARY

It has now been surprisingly discovered that transmucosal administration of Semaglutide across sublingual mucosa provides a viable alternative to SC injection and oral administration routes. Further, it has now been discovered that the active amount of Semaglutide administered daily or weekly for purposes of weight loss can be dramatically reduced from the typical 14 mg Semaglutide daily oral ingestion. Even more remarkable, it has now been discovered that the gastrointestinal side effects from daily ingestion of Semaglutide can be improved or minimized by incorporating a gastric peptide in combination with Semaglutide in a tablet for sublingual administration.

This disclosure includes sublingual Semaglutide compositions. In various embodiments, these compositions are in solid form, such as free-flowing powders, amenable to tableting in a tablet press.

In various embodiments, a sublingual Semaglutide composition comprises Semaglutide or a Semaglutide salt and a gastric peptide, in combination, and a carrier configured for a powdered composition amendable to compression into individual dosage tablets.

In various examples, a sublingual Semaglutide composition comprises Semaglutide sodium salt and BPC (Body Protection Compound) 157 acetate, in combination and formulated in single dose tablets configured for sublingual administration.

In various examples, a tablet for sublingual administration of Semaglutide comprises about 500 mcg active Semaglutide. In other examples, a higher dose tablet for sublingual administration of Semaglutide comprises about 750 mcg active Semaglutide.

In various embodiments, a weight loss regimen comprises sublingual administration to an individual in need thereof of a sublingual Semaglutide tablet comprising both Semaglutide or a Semaglutide salt, a gastric peptide, and a carrier comprising at least one excipient.

In various embodiments of the method, the individual in need thereof is diagnosed overweight and/or obese.

In various embodiments, a sublingual Semaglutide composition comprises from about 0.10 wt. % to about 0.40 wt. % of Semaglutide or salt thereof, from about 0.05 to about 0.15 wt. % of a gastric peptide or salt thereof, and a carrier, wherein the weight percentages are based on the total weight of the sublingual Semaglutide composition, and wherein the sublingual Semaglutide composition is in the physical form of a loose powder amendable to tableting by compression in a tablet press.

In various embodiments, a sublingual Semaglutide composition comprises from about 0.15 wt. % to about 0.30 wt. % Semaglutide sodium, based on the total weight of the sublingual Semaglutide composition.

In various embodiments, a sublingual Semaglutide composition comprises from about 0.05 wt. % to about 0.15 wt. % of Body Protection Compound-157 (BPC-157) acetate, based on the total weight of the sublingual Semaglutide composition.

In various embodiments, the carrier comprises a filler, a binder, a lubricant, a disintegrant, a glidant, or mixtures thereof.

In various embodiments, the carrier comprises a mixture of untreated fumed silica, sodium stearyl fumarate, microcrystalline cellulose, colloidal silicon dioxide, mannitol, fructose, and crospovidone.

In various embodiments, the carrier comprises from about 0.1 wt. % to about 5 wt. % of sodium stearyl fumarate.

In various embodiments, the carrier comprises from about 0.5 wt. % to about 1 wt. % untreated fumed silica.

In various embodiments, the carrier comprises up to about 30 wt. % crospovidone.

In various embodiments, a sublingual tablet for sublingual administration comprises from about 0.15 wt. % to about 0.30 wt. % of Semaglutide sodium, from about 0.05 to about 0.15 wt. % of BPC-157 acetate, and at least 99 wt. % of a carrier comprising untreated fumed silica, sodium stearyl fumarate, microcrystalline cellulose, colloidal silicon dioxide, mannitol, fructose and crospovidone, wherein the weight percentages are based on the total weight of the tablet.

In various embodiments, each tablet comprises about 250 mcg to about 1 mg Semaglutide sodium and about 300 mcg BPC-157 acetate.

In various embodiments, each tablet weighs approximately 275 mg.

In various embodiments, a method for suppressing appetite or for promoting weight loss in an individual in need thereof comprises sublingually administering to the individual a therapeutically effective amount of a sublingual Semaglutide composition comprising from about 0.15 wt. % to about 0.30 wt. % Semaglutide sodium; from about 0.05 to about 0.15 wt. % of BPC-157 acetate; and remainder, a carrier; wherein the weight percentages are based on the total weight of the sublingual Semaglutide composition.

In various embodiments, a therapeutically effective amount is an amount sufficient of the sublingual Semaglutide composition to deliver a total of from about 0.5 mg to about 21 mg active Semaglutide and from about 0.3 mg to about 8.4 mg active BPC-157 daily.

In various embodiments, a sublingual Semaglutide composition is in the physical form of individual sublingual tablets weighing approximately 275 mg each, and wherein the therapeutically effective amount of the sublingual Semaglutide composition comprises from about one (1) to about twenty eight (28) sublingual tablets daily.

In various embodiments, the individual in need thereof is diagnosed overweight or obese.

In various embodiments, a method for maintaining overall health, weight or BMI or for maintaining an overall healthy appearance in an individual in need thereof comprises sublingually administering to the individual a prophylactically effective amount of a sublingual Semaglutide composition comprising from about 0.15 wt. % to about 0.30 wt. % Semaglutide sodium; from about 0.05 to about 0.15 wt. % of BPC-157 acetate; and remainder, a carrier; wherein the weight percentages are based on the total weight of the sublingual Semaglutide composition.

In various embodiments, a prophylactically effective amount is an amount sufficient of the sublingual Semaglutide composition to deliver a total of from about 0.5 mg to about 21 mg active Semaglutide and from about 0.3 mg to about 8.4 mg active BPC-157 daily.

In various embodiments, a sublingual Semaglutide composition is in the physical form of individual sublingual tablets weighing approximately 275 mg each, and wherein the prophylactically effective amount of the sublingual Semaglutide composition comprises from about one (1) to about twenty eight (28) sublingual tablets daily

DETAILED DESCRIPTION

The detailed description of exemplary embodiments refers to the accompanying drawings, which show exemplary embodiments by way of illustration and best mode. While these exemplary embodiments are described in enough detail to enable those skilled in the art to practice the invention, other embodiments may be realized, and logical, chemical, and mechanical changes may be made without departing from the spirit and scope of the inventions. Thus, the detailed description is presented for purposes of illustration only and not of limitation. For example, unless otherwise noted, the steps recited in any of the method or process descriptions may be executed in any order and are not necessarily limited to the order presented. Furthermore, any reference to singular includes plural embodiments, and any reference to more than one component or step may include a singular embodiment or step. Also, any reference to attached, fixed, connected or the like may include permanent, removable, temporary, partial, full and/or any other possible attachment option. Additionally, any reference to without contact (or similar phrases) may also include reduced contact or minimal contact.

Sublingual Semaglutide compositions are described, along with dosage sizes and regimens, and methods of appetite suppression and weight loss using the compositions. In various embodiments, sublingual Semaglutide compositions are optimized for compression into single dose sublingual tablets configured for rapid disintegration and transmucosal permeation of Semaglutide across sublingual mucosa, allowing for a substantial reduction in Semaglutide actives amount necessary per day and minimization of gastrointestinal side effects.

In preferred embodiments, a sublingual Semaglutide composition is provided in a tablet dosage form for sublingual administration. In various examples, a sublingual Semaglutide composition is in the form of a loose or free-flowing powder that can be compressed in a tablet press into sublingual Semaglutide tablets weighing about 150 mg to about 350 mg and preferably about 275 mg.

Definitions

As used herein, the term "Semaglutide" refers to the GLP-1 receptor agonist developed by Novo Nordisk in 2012, described in U.S. Pat. No. 8,129,343 and assigned CAS No. 910463-68-2. The sodium salt of Semaglutide $(C_{187}H_{291}N_{45}O_{59} \cdot Na_x)$ is of interest and is referred to as "Semaglutide sodium salt" or more simply and interchangeably as "Semaglutide sodium" or "sodium Semaglutide." A method of preparing Semaglutide sodium salt at up to 99.69% purity is disclosed, for example, in Chinese Patent Publication No. CN114031680, published Feb. 11, 2022 to inventor Liu Zhiguo, filed Sep. 1, 2021 (Application No. CN202111020743) and assigned to ZHEJIANG PEPTITES BIOTECH CO LTD, incorporated herein by reference. Semaglutide sodium is commercially available, for example, from CYMIT QUIMICA, Barcelona, Spain, under the product reference number 3D-BS182652. For purposes herein, a given weight amount of Semaglutide sodium is approximated to provide essentially the same weight amount of active Semaglutide since the difference in molecular weight between Semaglutide and Semaglutide sodium is negligible.

As used herein, the term "gastric peptide" takes on its ordinary meaning in biochemistry and physiology, meaning an amino acid polymer exhibiting a desired physiological effect in the gut, such as an anti-inflammatory or ulcer healing efficacy. These gastric peptides can comprise naturally occurring peptides, fragments of naturally occurring peptides, or synthetic peptides that are not naturally occurring. Of interest here are gastric peptides that objectively or subjectively "heal the gut," such as those peptides known to decrease intestinal inflammation or heal wounds. Gastric peptides also include corresponding salts. Some examples of gastric peptides for use herein include, for example, ipamorelin (a pentapeptide displaying a high growth hormone releasing potency), CJC-1295 (or, DAC:GRF, a drug affinity complex/growth hormone-releasing factor comprising a 30-amino acid long synthetic peptide), BPC-157 (a penta-decapeptide, explained further below), Thymosin-$\beta_4$, a 43 amino acid long naturally occurring peptide, or KPV (a naturally occurring tripeptide), and salts of these peptides.

As used herein, the substance "BPC-157" refers to "body protection compound 157," a native gastric pentadecapeptide fragment of gastric juice BPC found naturally occurring. The peptide is nontoxic and has been shown to exhibit cytoprotective activity. It has been used in the treatment of ulcerative colitis and multiple sclerosis. Of interest herein is a BPC-157 salt, such as "BPC-157 acetate," a monoacetate salt of BPC-157 identified by CAS No. 1628202-19-6. Other salts of BPC-157 find use herein, such as "BPC-157 arginate." The sequence of BPC-157 is disclosed, for example, in U.S. Pat. Nos. 9,850,282 and 6,288,028. See also, P. Sikirid, et al., "Salutary and prophylactic effect of pentadecapeptide BPC 157 on acute pancreatitis and concomitant gastroduodenal lesions in rats," *Digestive Diseases and Sciences,* 41(7), 1518-1526, (1996). The acetate salt is available, for example, from Cayman Chemical, Ann Arbor, MI, under product number 30989. The present disclosure should not be seen as limited to just BPC-157 and its corresponding salts, as other gastric peptides, such as ipamorelin, CJC-1295, Thymosin-$\beta_4$, or KPV, or others yet to be discovered, may be found to mitigate the GI side effects of Semaglutide.

As used herein, the term "excipient" takes on its ordinary meaning in pharmaceutical compounding, namely the ingredients in a pharmaceutical composition other than drug actives (i.e., the inactive ingredients said to make up the composition of a "carrier"). In pharmaceutical tablets, excipients include, for example, diluents (sometimes called inert fillers), binders, disintegrants, lubricants, glidants, acidic agents, alkaline agents, pH buffering agents, colorings, flavorings, sweeteners, preservatives, surfactants, drug release-modifying agents, and coating materials. For sublingual tablets, drug release modifiers (such as to slow the release of a drug active in the gut) and tablet coatings (such as to ease swallowing) are not important, whereas disintegrants are important, seeing that a sublingual tablet generally needs to disintegrate under the tongue in a relatively short period of time and the drug actives need to absorb quickly. Some excipients used in tablet compositions may provide a benefit to the tableting process and overall manufacturing operation (e.g., binders and glidants). Certain excipients may promote flow of a powder into a tablet press, and/or optimize the compression process, tablet hardness, and so forth. It should be appreciated that certain chemical entities may provide multiple benefits, such as being both inert filler and a binding agent, and thus certain excipients for pharmaceutical tablets may fit into more than one functional group (filler, binder, disintegrant, etc.). For simplicity in describing the sublingual tablets herein, excipients may be said to be present in total in a "quantity sufficient" or "q. s." to bring a composition up to a total of 100 wt. %. The totality of the excipients may also be referred to as the "carrier" in a tablet composition. In various embodiments, a carrier herein comprises at least one excipient.

As used herein, the term "composition" takes on the ordinary meaning in formulation chemistry as a combination of ingredients. Simply written, a pharmaceutical composition may comprise one or more drug actives and a carrier, with the carrier comprising a suitable blend of excipients such that the final composition has the desired properties. In various embodiments, a composition is designed to adopt a particular physical form, or at least be amenable to physical manipulation into a desired physical form, which may be the dosage form for a particular treatment regimen. For example, a composition may be a free-flowing powder that by virtue of the selection of excipients, is amenable to tableting on a tablet press. Typically, a solid composition is made homogeneous by mixing or blending, such as in a ribbon blender, although not all powder compositions are white and/or homogeneous as to particle size distribution. In various embodiments, a composition herein comprises a powdered mixture amenable to compression on a tablet press into small tablets suitable for sublingual administration, wherein the administration route is characterized by rapid disintegration of the tablet under the tongue.

Ingredients for a composition herein are generally shown "as added," meaning there is a possibility for one or more chemical reactions between ingredients once the ingredients are mixed together, such as into a common carrier. One skilled in the art of formulation chemistry can recognize whether ingredients might react in a mixture. These reactions can include neutralization (e.g., between acid and alkali ingredients), mixed micelle formation (mixed surfactants in liquid systems) or other encapsulation phenomena, hydrolysis, and so forth. In various embodiments, ingredients in a composition are listed in "weight percent," (i.e., "wt. %"), based on the total weight of the composition. For example, 100 milligrams of a composition comprising 40 mg A and 60 mg B may be recited as "40 wt. % A and 60 wt. % B, based on the total weight of the composition," which necessarily totals to "100 wt. %." The actual weight amounts, (e.g., milligrams or grams) generally refers to amounts added for a particular batch size (e.g., a batch size of powder usable to make 100, 1000, or 10,000, or more, tablets).

As used herein, the term "dosage form" takes on its ordinary meaning in the pharmaceutical arts as the physical form of a composition designed for a particular administration route. For sublingual Semaglutide tablets, the dosage form is a tablet amenable to sublingual administration and disintegration. In various examples, an individual tablet herein may weigh from about 150 to about 350 mg, preferably about 275 mg, and each tablet may comprise from about 250 mcg to about 1000 mcg (1 mg) active Semaglutide, preferably about 500 mcg for a lower dose tablet and about 750 mcg for a higher dose tablet, with the remainder of each tablet comprising a carrier further comprising at least one excipient.

As used herein, the terms "subject," or "individual," or the phrases "a subject in need thereof," or "an individual in need thereof," refers to any human or non-human animal requiring or desirous of a pharmacological change. For example, a subject in need thereof may be a human patient clinically diagnosed with obesity, an eating disorder, or health issues relating to poor BMI, fat along the waistline, diet in general, or lack of exercise. In various embodiments, the subject in need thereof is a person desirous of a reduced appetite such that they can lose weight and/or improve health. Most importantly, a subject in need thereof can be any human in good health, but desirous of maintaining good health. In other words, the subject in need thereof may be desirous of a prophylactic regimen, like taking daily vitamins to prevent disease. The subject in need thereof may have the outward appearance of a person of average weight for their age, height and gender, but desirous of maintaining that weight, and thus desirous of curbing appetite in general.

As used herein, the term "treatment" of a subject (e.g., a human in need thereof) is any type of intervention used in an attempt to alter the natural course of the subject. Treatment includes, for example, administration of a sublingual Semaglutide composition and may be performed either prophylactically or subsequent to the initiation of a pathologic event or diagnosis of a physical issue, such as obesity. Also included are "prophylactic" treatments, which can be directed to reducing the rate of progression of obesity or condition being treated, delaying the onset of weight or condition, or reducing the severity of its onset. "Treatment" or "prophylaxis" does not necessarily indicate complete eradication, cure, or prevention of a disease or condition, or associated symptoms thereof. Treatment may also be entirely for cosmetic reasons, such as where an individual looks fit and has not received any diagnosis of a weight issue or a need for weight loss, but for whom maintaining a slim figure is believed desirous for some personal reason.

As used herein, the term "therapeutically effective amount" refers to a minimum dosage of a composition that provides a desired effect. Therefore, a therapeutically effective amount varies by subject, such as the physical condition of the individual and the need for medical intervention, dosage form, concentration of Semaglutide active in the composition, and the ultimate results desired. For example, a therapeutically effective amount of a 500 mcg Semaglutide sublingual tablet disclosed herein to treat an overweight individual, such as by suppressing the individual's appetite, might be on the order of one (1) to six (6) sublingual tablets daily, providing a total of about 0.5 to 3 mg active Semaglutide. In other examples, a therapeutically effective amount of a 500 mcg Semaglutide sublingual tablet disclosed herein to treat an obese individual might be on the order of six (6) to twenty eight (28) tablets daily, providing a total of about 3 to 14 mg active Semaglutide. In further examples, a therapeutically effective amount of a 750 mcg Semaglutide sublingual tablet disclosed herein to treat a morbidly obese individual plagued by constant hunger cravings might be on the order of six (6) to twenty eight (28) tablets daily, providing a total of about 4.5 to 21 mg active Semaglutide. Dosage regimens to treat overweight or medically obese individuals may vary depending on the weight and eating habits of the individual, such as if the individual experiences night cravings or breakthrough hunger.

As used herein, the term "prophylactically effective amount" refers to a minimum dosage of a composition that maintains an individual's present health status when taken regularly, such as an individual's current body weight and/or BMI. In various examples, an individual in need thereof may be an individual desirous of maintaining a healthy appearance. A prophylactically effective amount varies by subject, dosage form, concentration of Semaglutide active in the composition, and the habits and cravings of the individual. For example, a prophylactically effective amount of a 500 mcg Semaglutide sublingual tablet disclosed herein to suppress appetite cravings and help an individual maintain their current weight, BMI and/or overall health or appearance might be on the order of one (1) to six (6) sublingual tablets daily, providing a total of about 0.5 to 3 mg active Semaglutide.

As used herein, the term "modulate" includes to "increase" or "decrease" one or more quantifiable parameters, optionally by a defined and/or statistically significant amount. By "increase" or "increasing," "enhance" or "enhancing," or "stimulate" or "stimulating," refers generally to the ability of one or more sublingual Semaglutide compositions to produce or cause a greater physiological response (i.e., downstream effects) in a cell or in a subject relative to the response caused by either no Semaglutide composition or a control compound. Relevant physiological or cellular responses (in vivo or in vitro) upon administration of a sublingual Semaglutide tableted composition will be apparent to persons skilled in the art. An "increased" or "enhanced" amount is typically a "statistically significant" amount, and may include an increase that is 1.1, 1.2, 2, 3, 4, 5, 6, 7, 8, 9, 10, 15, 20, 30, 40, 50 or more times (e.g., 500, 1000 times), including all integers and decimal points in between and above 1 (e.g., 1.5, 1.6, 1.7. 1.8), the amount produced by no Semaglutide composition (the absence of a bioactive agent) or a control compound. The term "reduce" or "inhibit" may relate generally to the ability of one or more sublingual Semaglutide compositions to "decrease" a relevant physiological or cellular response, such as a symptom of a disease like obesity or a condition like excessive weight described herein, as measured according to routine techniques in the diagnostic art. Relevant physiological or cellular responses (in vivo or in vitro) will be apparent to persons skilled in the art, and may include reductions in the symptoms or pathology of a disease such as obesity and related issues like inflammation or pain. A "decrease" in a response may be "statistically significant" as compared to the response produced by no sublingual Semaglutide composition or a control composition, and may include a 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% decrease, including all integers in between.

As used herein, the term "approximately" in reference to amounts refers to plus or minus 5% of the value given, such as wt. %. The term "about," a in reference to amounts refers to plus or minus 10% of the value given, such as wt. %.

General Embodiments

Drug Actives

In various embodiments, a sublingual Semaglutide composition comprises Semaglutide or a Semaglutide salt and a gastric peptide, wherein the sublingual Semaglutide composition is in the form of a free-flowing powder that is amenable to tableting. It has now been found that a gastric peptide, such as BPC-157, improves and/or minimizes the GI tract side effects of Semaglutide.

In various embodiments, a sublingual Semaglutide composition comprises from about 0.10 wt. % to about 0.40 wt. % Semaglutide or a Semaglutide salt, or more preferably, from about 0.15 wt. % to about 0.30 wt. %, based on the total weight of the sublingual Semaglutide composition. In some preferred embodiments, a lower dose sublingual Semaglutide composition comprises from about 0.15 wt. % to about 0.20 wt. % Semaglutide or a Semaglutide salt, based on the total weight of the sublingual Semaglutide composition. In these related lower dose examples, a sublingual Semaglutide composition comprises from about 0.15 wt. % to about 0.20 wt. % Semaglutide sodium, based on the total weight of the sublingual Semaglutide composition. In other preferred embodiments, a higher dose sublingual Semaglutide composition comprises from about 0.20 wt. % to about 0.30 wt. % Semaglutide or a Semaglutide salt, based on the total weight of the sublingual Semaglutide composition. In these related higher dose examples, a sublingual Semaglutide composition comprises from about 0.20 wt. % to about 0.30 wt. % Semaglutide sodium, based on the total weight of the sublingual Semaglutide composition.

In various embodiments, a sublingual Semaglutide composition comprises from about 0.05 wt. % to about 0.15 wt. % of a gastric peptide, based on the total weight of the sublingual Semaglutide composition. In various examples, the gastric peptide is one or a combination of ipamorelin, CJC-1295, BPC-157, Thymosin-$\beta_4$, or KPV, or their corresponding salts.

In various embodiments, a sublingual Semaglutide composition comprises from about 0.05 wt. % to about 0.15 wt.

% BPC-157 or a BPC-157 salt, based on the total weight of the sublingual Semaglutide composition. In preferred embodiments, a sublingual Semaglutide composition comprises from about 0.05 wt. % to about 0.15 wt. % BPC-157 acetate, based on the total weight of the sublingual Semaglutide composition.

In various embodiments, a sublingual Semaglutide composition comprises from about 0.10 wt. % to about 0.40 wt. % Semaglutide sodium, and from about 0.05 wt. % to about 0.15 wt. % BPC-157 acetate, based on the total weight of the sublingual Semaglutide composition.

In various embodiments, a sublingual Semaglutide composition comprises from about 0.15 wt. % to about 0.30 wt. % Semaglutide sodium, and from about 0.05 wt. % to about 0.15 wt. % BPC-157 acetate, based on the total weight of the sublingual Semaglutide composition.

In various embodiments, a low dose sublingual Semaglutide composition comprises from about 0.15 wt. % to about 0.20 wt. % Semaglutide sodium, and from about 0.05 wt. % to about 0.15 wt. % BPC-157 acetate, based on the total weight of the sublingual Semaglutide composition.

In various embodiments, a high dose sublingual Semaglutide composition comprises from about 0.20 wt. % to about 0.30 wt. % Semaglutide sodium, and from about 0.05 wt. % to about 0.15 wt. % BPC-157 acetate, based on the total weight of the sublingual Semaglutide composition.

In various examples, the remainder of a sublingual Semaglutide composition that comprises both Semaglutide or salt thereof and a gastric peptide or salt thereof, is a carrier. In various embodiments, a carrier comprises at least one excipient.

Carrier

In various embodiments, a sublingual Semaglutide composition comprises at least 90 wt. %, at least 95 wt. %, or at least 99 wt. % of a carrier, based on the total weight of the sublingual Semaglutide composition. In certain examples, a sublingual Semaglutide composition comprises >99.0 wt. %, >99.1 wt. %, >99.2 wt. %, >99.3 wt. %, >99.4 wt. %, >99.5 wt. %, >99.6 wt. %, or >99.7 wt. % of a carrier, based on the total weight of the sublingual Semaglutide composition. A carrier for a sublingual Semaglutide composition is a solid substance, or more preferably, a mixture of solid substances that can be in the form of a loose powder.

In certain examples, a carrier for a sublingual Semaglutide composition comprises any combination of filler, binder, disintegrant, lubricant, glidant, surfactant, acidic agent, alkaline agent, pH buffering agent, preservative, drug release modifier, coating material, coloring, flavoring, and sweetener, totaling at least 90 wt. %, at least 95 wt. %, or preferably, at least 99 wt. % of the total weight of the sublingual Semaglutide composition.

In certain embodiments, a carrier for a sublingual Semaglutide composition comprises a filler and a disintegrant. In most cases, the filler represents the majority of the weight of a carrier.

In certain examples, a carrier for a sublingual Semaglutide composition comprises a filler, a lubricant, a glidant, and a disintegrant, where the filler represents the majority of the weight of a carrier.

Filler (Diluent)

In various embodiments, a carrier for a sublingual Semaglutide composition comprises a filler. In certain examples, the filler will comprise the majority of the carrier by wt. %. Fillers include, for example, colloidal anhydrous silica (e.g., Aerosil® 200 or 300 Pharma, or Aeroperl® 300 Pharma), magnesium aluminometasilicate (Neusilin® US2), calcium silicate (Florite®), microcrystalline cellulose powder (e.g., Avicel® PH101 or PH102), silicified microcrystalline cellulose (PROSOLV® SMCC), various starches, and various sugars. Commonly used fillers in pharmaceutical powders and tablets include microcrystalline cellulose (MCC) and/or silicified microcrystalline cellulose (SMCC), and/or a simple sugar, such as mannitol, fructose, or lactose, or combinations of a cellulose and a simple sugar, such as a combination of microcrystalline cellulose and fructose (with either one as the majority wt. %). In various embodiments, a combination of MCC and colloidal silicon dioxide (e.g., 98:2) can substitute for SMCC, although there is some evidence the physical mixture results in some sticking of die punches (see, A. Aljaberi, et al., "Functional performance of silicified microcrystalline cellulose versus microcrystalline cellulose: a case study," *Drug Dev. Ind. Pharma.*, 35(9), 1066-1071, (2009)).

Other fillers that may find use in sublingual Semaglutide compositions of the present disclosure include, for example, cellulose acetate, sorbitol, sucrose, dextrin, dextrose, calcium phosphate dibasic, calcium carbonate, maltose, maltodextrin, kaolin, tribasic calcium phosphate, calcium sulfate, cellulose acetate butyrate (cellaburate), calcium lactate, cellulose acetate, erythritol, ethyl cellulose, ethyl acrylate/methyl methacrylate copolymer, isomalt, α-lactalbumin, lactitol, magnesium carbonate, magnesium oxide, methacrylic acid/ethyl acrylate copolymer, methacrylic acid/methyl methacrylate copolymer, polydextrose, sodium chloride, simethicone, hydrogenated pullulan, talc, amino methacrylate copolymer, trehalose, and xylitol.

In various embodiments, a carrier for a sublingual Semaglutide composition comprises a combination of microcrystalline cellulose, colloidal silicon dioxide, mannitol and fructose as a filler, at a level of from about 70 wt. % to about 99 wt. %, based on the total weight of the sublingual Semaglutide composition.

Lubricant

In various embodiments, a carrier for a sublingual Semaglutide composition comprises a lubricant. Examples of a lubricant include, for example, magnesium stearate, calcium stearate, zinc stearate, sodium lauryl sulfate, sodium stearyl fumarate (SSF), magnesium lauryl sulfate, stearic acid, glyceryl behenate, behenoyl polyoxyl glycerides (e.g., Compritol® HD5), glyceryl dibehenate, lauric acid, glyceryl monostearate, glyceryl tristearate, myristic acid, palmitic acid, poloxamer, polyethylene glycol, polysorbate 20, polyoxyl-10-oleyl ether, polyoxyl-15-hydroxystearate, polysorbate 40, polyoxyl-20-cetostearyl ether, polyoxyl-40-stearate, polysorbate 60, polysorbate 80, potassium benzoate, sodium benzoate, sorbitan monolaurate, sorbitan monooleate, sodium stearate, sorbitan monopalmitate, sorbitan monostearate, zinc stearate, sorbitan sesquioleate, sorbitan trioleate, and talc.

In various embodiments, a carrier for a sublingual Semaglutide composition comprises sodium stearyl fumarate (SSF) as a tablet lubricant at a level of from about 0.1 wt. % to about 5 wt. %, based on the total weight of the sublingual Semaglutide composition. SSF is available, for example, from JRS Pharma under the trade name PRUV®, or from SPI Pharma under the brand name Lubripharm® SSF.

Binder

In various embodiments, a carrier for a sublingual Semaglutide composition comprises a binder. Examples of a binder include, for example, polyvinylpyrrolidone (PVP, or povidone), crosslinked polyvinylpyrrolidone (crospovidone) vinylpyrrolidone-vinyl acetate copolymer (copovidone), carbomer, polyethylene glycol (PEG), starches and starch derivatives such as corn starch, pregelatinized starch, carboxymethylcellulose (carmellose), hydroxypropyl methylcellulose (hypromellose), cellulose ethers (e.g., Methocel™) hydroxyethyl cellulose, hydroxypropyl cellulose, hydroxyethyl methyl cellulose, calcium carboxymethylcellulose, calcium cellulose glycolate, ethyl cellulose, chitosan, dextrin, inulin, magnesium aluminum silicate, maltodextrin, methylcellulose, dextrates, sodium alginate, zein, gelatin, polymethacrylates, sorbitol, and acacia.

In various embodiments, a carrier for a sublingual Semaglutide composition comprises from none to up to about 20 wt. % binder.

Disintegrant

In various embodiments, a carrier for a sublingual Semaglutide composition comprises a disintegrant. Examples of a disintegrant include, for example, crospovidone, croscarmellose sodium, sodium starch glycolate, crosslinked sodium carboxymethyl cellulose, low-substituted hydroxypropylcellulose, guar gum, chitosan hydrochloride, calcium alginate, sodium alginate, docusate sodium, magnesium aluminum silicate, methylcellulose, calcium carboxymethylcellulose, and calcium cellulose glycolate.

In various embodiments, a carrier for a sublingual Semaglutide composition comprises crospovidone as a disintegrant at a level of from about 0.1 wt. % to about 30 wt. %, based on the total weight of the sublingual Semaglutide composition. In certain examples, a sublingual Semaglutide composition for tableting comprises from about 2 wt. % to about 5 wt. % crospovidone as the disintegrant, based on the total weight of the sublingual Semaglutide composition.

Glidants

In various embodiments, a carrier for a sublingual Semaglutide composition comprises a glidant. Examples of a glidant include, for example, untreated fumed silica (e.g., CAB-O-SIL® M-5P or M-5DP), colloidal silicon dioxide, talc, tribasic calcium phosphate, calcium silicate, magnesium oxide, sodium stearate, magnesium silicate, magnesium trisilicate, and hydrophobic colloidal silica. In preferred embodiments, untreated fumed silica is included in a carrier for a sublingual Semaglutide composition as a glidant for improving tablet production.

In various embodiments, a carrier for a sublingual Semaglutide composition comprises untreated fumed silica as a glidant at a level of from about 0.5 wt. % to about 1 wt. %, based on the total weight of the sublingual Semaglutide composition. The untreated fumed silica acts as a free-flow agent to improve tablet production efficiencies, tablet uniformity, and tablet hardness.

In various embodiments, a carrier for a sublingual Semaglutide composition consists essentially of a mixture of untreated fumed silica, sodium stearyl fumarate, microcrystalline cellulose, colloidal silicon dioxide, mannitol, fructose and crospovidone, at a total level of at least 99 wt. %, based on the total weight of the sublingual Semaglutide composition.

In various embodiments, a commercially available carrier for use in pharmaceutical tablets may be used as all or part of a carrier in a sublingual Semaglutide composition in accordance with the present disclosure. For example, PROSOLV® ODT G2 may be used as the carrier or as the majority of a carrier by weight for sublingual Semaglutide compositions for tableting in accordance with the present disclosure. This commercial product, having a bulk density of about 0.45-0.65 g/mL, comprises a mixture of microcrystalline cellulose, colloidal silicon dioxide, mannitol, fructose, and crospovidone, and is available from JRS Pharma, Cedar Rapids, IA.

In various embodiments, a carrier for a sublingual Semaglutide composition comprises at least 85 wt. % or at least 90 wt. % of PROSOLV® ODT G2. In certain examples, a carrier for a sublingual Semaglutide composition comprises at least 85 wt. %, at least 86 wt. %, at least 87 wt. %, at least 88 wt. %, at least 89 wt. %, or at least 90 wt. % PROSOLV® ODT G2. In various embodiments, a carrier for a sublingual Semaglutide composition comprises at least 90 wt. % of PROSOLV® ODT G2 along with about 0.5 wt. % to 1 wt. % untreated fumed silica and about 0.1 wt. % to about 5 wt. % sodium stearyl fumarate. In various formulations, the weight percentage of PROSOLV® ODT G2 may be indicated simply as "quantity sufficient," or "q.s." In some examples, the amount of this carrier can be adjusted accordingly to accommodate changes in formulation, such as for example, presence or absence of a flavoring agent or higher or lower Semaglutide actives levels.

A carrier comprising mostly PROSOLV® ODT G2 by weight may also include other separately added fillers, binders, lubricants, disintegrants, and/or glidants as necessary to optimize tablet processing and tablet properties.

Other Excipients

In various embodiments, a carrier of a sublingual Semaglutide composition further comprises any combination of flavoring agent, masking agent, and/or sweetener, with the combination present at from about 0.1 wt. % to about 15 wt. %, based on the total weight of the sublingual Semaglutide composition, recognizing that these levels depend on the combination chosen, and the types of ingredients, to mask certain unpleasant tastes and to make the overall experience of sublingual administration acceptable to the user. In some instances, a combination of sucralose (granular) at from about 0.1 wt. % to about 0.5 wt. % and flavoring agent such as peppermint powder at from about 2.5 wt. % to about 7.5 wt. % suffices to mask any unpleasant taste of the sublingual Semaglutide composition and make the product overall acceptable to users in taste panels.

In various embodiments, a sublingual Semaglutide composition includes a sweetener such as sucralose but no flavoring agent.

In various embodiments, a carrier for a sublingual Semaglutide composition comprises a sweetener. Examples of a sweetener include, for example, *stevia*, aspartame, sucralose, acesulfame, or saccharin. In other examples, a sweetener for sublingual Semaglutide compositions may be a common sugar or sugar alcohol typically used in sweetening foods and medicines, such as sucrose, fructose, glucose, lactose, xylitol, mannitol, sorbitol, erythritol, and syrups therefrom, and so forth, noting that some of these substances find use in tablet compositions as fillers, and a composition may be deemed sweet tasting enough simply from the filler including a sugar. Any of the natural and artificial sweeteners, alone or in combination, are used in the sublingual Semaglutide compositions at a total wt. % level sufficient to provide a consumer acceptable experience when using the sublingual Semaglutide composition. For a review of these concepts, see H. Sohi, "Taste Masking Technologies in Oral Pharmaceuticals: Recent Developments and Approaches," *Drug Development and Industrial Pharmacy,* 30(5), 429-448 (2004).

In various embodiments, a carrier for a sublingual Semaglutide composition comprises any one or combination of flavoring agent, sweetener, buffer (or acidic agent and/or alkali agent), colorant, transmucosal permeation enhancer, stabilizer, preservative, or other pharmaceutically acceptable excipient. Any of these materials not specifically mentioned herein may be found in "Handbook of Pharmaceutical Excipients, 6$^{th}$ Edition, R. C Rowe, et al., editors, Pharmaceutical Press, London, 2009.

Suitable flavoring agents can include, for example, flavors, such as, natural flavors, artificial flavors, and combinations thereof. Non-limiting examples of flavor oils include spearmint oil, cinnamon oil, oil of wintergreen (methyl salicylate), peppermint oil, clove oil, bay oil, anise oil, eucalyptus oil, thyme oil, cedar leaf oil, oil of nutmeg, allspice, oil of sage, mace, oil of bitter almonds, and cassia oil. Suitable flavoring agents also include, for example, artificial, natural and synthetic fruit flavors such as vanilla, citrus oils (e.g., lemon, orange, lime, and grapefruit), and fruit essences (e.g., apple, pear, peach, grape, strawberry, raspberry, cherry, plum, pineapple, and apricot), and the like, and combinations thereof. Many oil flavorings are available absorbed onto powdered carriers for ease of use in powder formulations, or oils can be adsorbed into a mixture of powders being mixed in a blender, such as by addition through a spray bar configured within a ribbon mixer. In other examples, such as powdered peppermint, the leaves of the plant are dried and finely powdered, and that resulting powder used in pharmaceutical compositions.

Other flavoring agents and fragrant aromatics that may be included individually or in combination include, for example, anethole, menthol, menthone, menthyl acetate, eucalyptol, borneol, borneol acetate, camphor, 1,8-cineole, cinnamaldehyde, benzaldehyde, citral, thujone, eugenol, limonene, geraniol, citronellol, citronellal, pinene, linalool, thymol, carvone, caryophyllene, linalyl acetate, methyl salicylate, and mixtures thereof. Also, substances that provide scent and flavor include, for example, 3,3,5-trimethyl-cyclohexanol, methoxycyclohexanol, benzyl alcohol, anise alcohol, cinnamyl alcohol, 0-phenyl ethyl alcohol (2-phenylethanol), cis-3-hexenol, musk xylol, isoeugenol, methyl eugenol, α-amylcinnamic aldehyde, anisaldehyde, n-butyl aldehyde, cumin aldehyde, cyclamen aldehyde, decanal, isobutyl aldehyde, hexyl aldehyde, heptyl aldehyde, n-nonyl aldehyde, nonadienol, hydroxycitronellal, benzaldehyde, methyl nonyl acetaldehyde, dodecanol, α-hexylcinnamic aldehyde, undecenal, heliotropin, vanillin, ethyl vanillin, methyl amyl ketone, methyl 0-naphthyl ketone, methyl nonyl ketone, musk ketone, diacetyl, acetyl propionyl, acetyl butyryl, acetophenone, p-methyl acetophenone, ionone, methyl ionone, amyl butyrolactone, diphenyl oxide, methyl phenyl glycidate, γ-nonyl lactone, coumarin, cineole, ethyl methyl phenyl glycidate, methyl formate, isopropyl formate, linalyl formate, ethyl acetate, octyl acetate, methyl acetate, benzyl acetate, butyl propionate, isoamyl acetate, isopropyl isobutyrate, geranyl isovalerate, allyl capronate, butyl heptylate, octyl caprylate octyl, methyl heptynecarboxylate, methine octynecarboxylate, isoacyl caprylate, methyl laurate, ethyl myristate, methyl myristate, ethyl benzoate, benzyl benzoate, methylcarbinylphenyl acetate, isobutyl phenylacetate, methyl cinnamate, cinnamyl cinnamate, ethyl anisate, methyl anthranilate, ethyl pyruvate, ethyl α-butyl butylate, benzyl propionate, butyl acetate, butyl butyrate, p-tert-butylcyclohexyl acetate, cedryl acetate, citronellyl acetate, citronellyl formate, p-cresyl acetate, ethyl butyrate, ethyl caproate, ethyl cinnamate, ethyl phenylacetate, ethylene brassylate, geranyl acetate, geranyl formate, isoamyl salicylate, isoamyl isovalerate, isobornyl acetate, linalyl acetate, methyl anthranilate, methyl dihydrojasmonate, β-phenylethyl acetate, trichloromethylphenyl carbinyl acetate, terpinyl acetate, vetiveryl acetate, and mixtures thereof. Some of these compounds are going to function as masking agents, and there is no attempt here to distinguish from what might purely be a flavoring agent and what might purely be a masking agent since a masking agent is likely to have some flavor profile.

Suitable buffers may comprise one or more acidifying agents or alkaline agents as necessary to neutralize various co-ingredients, form salts of various co-ingredients, and/or achieve a particular pH target for the composition, such as to adjust the local environment in the oral cavity. Combinations of various acidifying agents and alkaline agents may be used to create buffering systems that stabilize the desired final pH of an aqueous solution formed from a powdered composition. Buffers may be mixed buffers, meaning that the alkaline agent is not necessarily the conjugate base of the acidifying agent.

Exemplary acidifying agents for use in the present compositions include, for example, organic acids of any molecular weight and mineral acids (inorganic acids such as HCl), and mixtures thereof. Organic acids may include mono-carboxylic acids, di-carboxylic acids, or tri-carboxylic acids, and may be saturated or may have any degree of unsaturation. For example, organic acids for use in various embodiments of the composition in accordance to the present disclosure may include, for example, formic acid, carbonic acid, acetic acid, lactic acid, oxalic acid, propionic acid, valeric acid, enanthic acid, pelargonic acid, butyric acid, lauric acid, docosahexaenoic acid, eicosapentaenoic acid, pyruvic acid, acetoacetic acid, benzoic acid, salicylic acid, aldaric acid, fumaric acid, glutaconic acid, traumatic acid, muconic acid, malonic acid, malic acid, succinic acid, glutaric acid, adipic acid, pimelic acid, suberic acid, azelaic acid, abietic acid, pimaric acid, sebacic acid, phthalic acid, isophthalic acid, terephthalic acid, maleic acid, citric acid, and combinations thereof.

Exemplary alkaline materials include any organic amines, $NH_3$, alkali metal or alkaline earth hydroxide, any conjugate bases of any organic acids (e.g. R—COO$^-$), and any of the salts of carbonic acid, phosphoric acid, nitric acid and sulfuric acid, and any mixtures thereof. For example, alkaline materials for use in various embodiments of the composition may include, for example, NaOH, KOH, sodium acetate, sodium succinate, disodium succinate, monosodium citrate, disodium citrate, trisodium citrate, $NaH_2PO_4$, $Na_2HPO_4$, $Na_3PO_4$, $KH_2PO_4$, $K_2HPO_4$, $K_3PO_4$, $NaHSO_4$, $Na_2SO_4$, $KHSO_4$, $K_2SO_4$, $NaHCO_3$, $Na_2CO_3$, $KHCO_3$, $K_2CO_3$, $NaH_3P_2O_7$, $Na_2H_2P_2O_7$, $Na_3HP_2O_7$, $Na_4P_2O_7$, $KH_3P_2O_7$, $K_2H_2P_2O_7$, $K_3HP_2O_7$, $K_4P_2O_7$, and mixtures thereof. Any of these chemical species may exist as various hydrates when purchased as raw materials for use in the present compositions.

Exemplary colorants include the pharmaceutically acceptable colors used for powdered and tableted pharmaceutical dosage forms, such as the United States Food & Drug Administration (FDA) certified colors for use in pharmaceutical compositions. Examples include FD&C colors and some D&C colors. These colorants, if even found necessary to include in the powdered sublingual Semaglutide compositions for tableting, are simply for aesthetic reasons. In various examples, sublingual Semaglutide tablets comprise no colorants, and appear white or slightly off-white from the color of the filler.

In various embodiments, sublingual Semaglutide compositions may also include a transmucosal permeation enhancer to accelerate absorption of the Semaglutide or Semaglutide salt, and/or the gastric peptide sublingually. Suitable transmucosal permeation enhancers include, for example, surfactants that assist bio-absorption, including, for example, fatty acids and/or esters or salts thereof, bile acids and/or salts thereof. In some instances, a permeation enhancer may be a polysorbate or sorbate ester. For a review of transmucosal permeation enhancers that find use herein, see B. Aungst, "Comparison of the effects of various trans-mucosal absorption promoters on buccal insulin delivery," *International Journal of Pharmaceutics,* 53(3), 227-235 (1989).

Stabilizers and preservatives for oral compositions include the parabens, sorbitol, sodium benzoate, benzoic acid, sorbic acid, potassium sorbate, propionic acid, and combinations thereof. Antioxidants include, for example, Vitamin C, Vitamin E, butylated hydroxyanisole (BHA), butylated hydroxytoluene (BHT), and propylgallate. For a review see, I. Himoudy, "Preservatives and their role in pharma and clinical research," *International Journal of Pharma Sciences and Scientific Research,* 2:4, 134-151 (2016).

TABLE 1 sets forth general embodiments of a sublingual Semaglutide composition. The compositions are in the physical form of a powder, and the embodiments within these ranges are powders that are amendable to tableting into hard tablets in a tablet press.

TABLE 1

Sublingual Semaglutide Compositions

| Ingredient (wt. %) | Preferred wt. % ranges |
|---|---|
| Semaglutide or salt thereof | 0.10 to 0.40 |
| Gastric peptide or salt thereof | 0.05 to 0.15 |

TABLE 1-continued

Sublingual Semaglutide Compositions

| Ingredient (wt. %) | Preferred wt. % ranges |
|---|---|
| Glidant | 0.5 to 1.0 |
| Lubricant | 0.1 to 5 |
| Flavoring and/or masking agent | 0 to 7.5 |
| Filler and disintegrant mixture[1] | q. s. |
| Total | 100 wt. % |
| Physical Appearance | Free-flowing powder |
| Transmucosal route of administration | Sublingual in tablet form |
| Recommended tablet weight | 150-350 mg |
| Preferred tablet weight | 275 mg |
| Preferred active Semaglutide per 275 mg sublingual tablet | 500 mcg or 750 mcg |
| Preferred active gastric peptide per 275 mg sublingual tablet | 300 mcg |

TABLE 1 notes:

[1]In various embodiments, this filler and disintegrant mixture may comprise a mixture of microcrystalline cellulose, colloidal silicon dioxide, mannitol, fructose, and crospovidone, available for example under the trade name PROSOLV ® ODT G2 from JRS Pharma, Cedar Rapids, IA. In some instances, the microcrystalline cellulose and colloidal silicon dioxide can be replaced by silicified microcrystalline cellulose.

Exemplary Compositions, Dosage Forms, and Methods of Administration

Table 2 sets forth preferred compositions for a sublingual Semaglutide composition, namely a low dose example both flavored and unflavored and a high dose example both flavored and unflavored. The example compositions are loose powders proven amendable to tableting into 275 mg tablets using a standard tablet press, as detailed below.

TABLE 2

Exemplary Sublingual Semaglutide Compositions and Dosages:

| Ingredients (in wt. %) | Low Dose Flavored | Low Dose Unflavored | High Dose Flavored | High Dose Unflavored |
|---|---|---|---|---|
| Semaglutide Sodium | 0.18 | 0.18 | 0.27 | 0.27 |
| BPC-157 acetate | 0.11 | 0.11 | 0.11 | 0.11 |
| Silica, untreated fumed | 0.73 | 0.73 | 0.73 | 0.73 |
| Sodium stearyl fumarate | 2.73 | 2.73 | 2.73 | 2.73 |
| PROSOLV ® ODT G2[2] | 90.44 | 95.89 | 90.35 | 95.80 |
| Sucralose, granular | 0.36 | 0.36 | 0.36 | 0.36 |
| Peppermint (powdered) | 5.45 | -0- | 5.45 | -0- |
| Total | 100.00 | 100.00 | 100.00 | 100.00 |
| Appearance | White powder | White powder | White powder | White powder |
| Tablet after tableting in a tablet press | 275 mg white tablets | 275 mg white tablets | 275 mg white tablets | 275 mg white tablets |
| Active Semaglutide per tablet | 500 mcg | 500 mcg | 750 mcg | 750 mcg |
| Active BPC-157 peptide per tablet | 300 mcg | 300 mcg | 300 mcg | 300 mcg |

TABLE 2 notes:

[2]PROSOLV ODT G2 provides a mixture of microcrystalline cellulose, colloidal silicon dioxide, mannitol, fructose, and crospovidone, wherein the combined amount of microcrystalline cellulose, colloidal silicon dioxide, mannitol and fructose is about 95 wt. % to about 98 wt. % of the PROSOLV ® ODT G2 mixture and wherein the amount of crosprovidone is about 2 wt. % to about 5 wt. % of the PROSOLV ® ODT G2 mixture.

The compositions of Tables 1 and 2 are produced by simple mixing in accordance with the following procedure:

All ingredients are combined and mixed in a V-blender for about 45 minutes or until a homogenous free-flowing powder is obtained. For tableting, the powder is placed in the hopper of a Natoli NP-255 Production Tablet Press or a Stokes Model 511 tablet press calibrated to produce tablets weighing approximately 275 mg each. The results of the tableting process are hard white tablets.

In various embodiments, a dose of a sublingual Semaglutide composition and comprising from about 0.15 wt. % to about 0.30 wt. % Semaglutide sodium based on the total weight of the composition is about 150 mg to about 350 mg, preferably about 275 mg. In various embodiments, the dose is an individual tablet weighing about 150 mg to about 350 mg, or preferably about 275 mg.

In various embodiments, a dose of a 275 mg sublingual Semaglutide tablet provides about 500 mcg Semaglutide.

In various embodiments, a dose of a 275 mg sublingual Semaglutide tablet provides about 750 mcg Semaglutide In various embodiments, a dose of a sublingual Semaglutide composition and comprising from about 0.05 wt. % to about 0.15 wt. % BPC-157 acetate based on the total weight of the composition is about 150 mg to about 350 mg, preferably about 275 mg. In various embodiments, the dose is an individual tablet weighing about 150 mg to about 350 mg, or preferably about 275 mg.

In various embodiments, a dose of a 275 mg sublingual Semaglutide tablet provides about 500 mcg Semaglutide and about 300 mcg BPC-157 in combination.

In various embodiments, a dose of a 275 mg sublingual Semaglutide tablet provides about 750 mcg Semaglutide and about 300 mcg BPC-157 in combination.

Dosage Regimens and Dosage Amounts

In various embodiments, methods for (a) suppressing appetite in an individual in need thereof, (b) losing weight in obese or overweight individuals in need thereof, such as those clinically diagnosed as overweight or obese, and (c) maintaining a healthy weight or desired appearance in an individual in need thereof, are described.

In various embodiments, an individual in need thereof has been diagnosed as overweight or obese, as per ICD-10 code E66 and subgroups. This diagnosis is discussed in S. B. Gribsholt, et al., "Validity of ICD-10 diagnoses of overweight and obesity in Danish hospitals," *Clin. Epidemiol.*, 11, 845-854 (2019). These individuals in need thereof may seek therapeutic treatments of their obesity with a weight loss regimen comprising sublingual Semaglutide tablets in accordance with the present disclosure.

In various embodiments, a method for suppressing appetite in an individual in need thereof comprises sublingually administering to the individual a therapeutically effective amount of a sublingual Semaglutide composition. In various examples, the individual in need thereof is clinically diagnosed as overweight or obese.

In various embodiments, the therapeutically effective amount of the sublingual Semaglutide composition comprises an amount sufficient to sublingually provide from about 0.5 mg to about 21 mg of active Semaglutide daily. This daily regimen is continued for a time necessary to obtain a desired outcome. In various examples, the therapeutically effective amount of the sublingual Semaglutide composition comprises from one (1) to up to twenty eight (28) 275 mg sublingual Semaglutide tablets daily, wherein each 275 mg tablet provides about 500 mcg Semaglutide and about 300 mcg BPC-157 in combination. In other examples, the therapeutically effective amount of the sublingual Semaglutide composition comprises from one (1) to up to twenty eight (28) 275 mg sublingual Semaglutide tablets daily, wherein each 275 mg tablet provides about 750 mcg Semaglutide and about 300 mcg BPC-157 in combination In various embodiments, a method of promoting weight loss in an individual in need thereof comprises sublingually administering to the individual a therapeutically effective amount of a sublingual Semaglutide composition. In various examples, the individual in need thereof is clinically diagnosed as overweight or obese. In various embodiments, the therapeutically effective amount of the sublingual Semaglutide composition comprises an amount sufficient to sublingually provide from about 0.5 mg to about 21 mg of active Semaglutide daily. This daily regimen is continued for a time necessary to obtain a desired outcome. In various examples, the therapeutically effective amount of the sublingual Semaglutide composition comprises from one (1) to up to twenty eight (28) 275 mg sublingual Semaglutide tablets daily, wherein each 275 mg tablet provides about 500 mcg Semaglutide and about 300 mcg BPC-157 in combination. In other examples, the therapeutically effective amount of the sublingual Semaglutide composition comprises from one (1) to up to twenty eight (28) 275 mg sublingual Semaglutide tablets daily, wherein each 275 mg tablet provides about 750 mcg Semaglutide and about 300 mcg BPC-157 in combination In various embodiments, a method for maintaining overall health, weight or BMI or for maintaining an overall healthy appearance in an individual in need thereof comprises sublingually administering to the individual a prophylactically effective amount of a sublingual Semaglutide composition. In various examples, the individual in need thereof is not clinically diagnosed as overweight or obese, but instead desires maintenance of a certain physical appearance or overall healthy state. In various embodiments, the prophylactically effective amount of the sublingual Semaglutide composition comprises an amount sufficient to sublingually provide a total of about 0.5 to 3 mg active Semaglutide daily. This daily regimen is continued for a time necessary to obtain a desired outcome, which in the case of maintaining overall health and weight, might be indefinitely, i.e., throughout the life of the individual. In various examples, the prophylactically effective amount of the sublingual Semaglutide composition comprises from one (1) to about six (6) 275 mg sublingual Semaglutide tablets daily, wherein each 275 mg tablet provides about 500 mcg Semaglutide and about 300 mcg BPC-157 in combination. In various embodiments, a fewer number of a high dose tablet may be used for maintaining an overall healthy appearance in an individual. In various examples, the prophylactically effective amount of the sublingual Semaglutide composition comprises from one (1) to about four (6) 275 mg sublingual Semaglutide tablets daily, wherein each 275 mg tablet provides about 750 mcg Semaglutide and about 300 mcg BPC-157 in combination.

A dose of a sublingual Semaglutide composition herein is from about 150 mg to about 350 mg, preferably about 275 mg of a composition, with a single dose preferably comprising a single sublingually administered tablet. A single 275 mg dose of a sublingual Semaglutide composition in the form of a tablet preferably provides about 500 mcg active Semaglutide and about 300 mcg BPC-157 peptide in combination, or about 750 mcg active Semaglutide and about 300 mcg BPC-157 peptide in combination. Thus, for example, three (3) 275 mg doses of a low dose sublingual Semaglutide composition (i.e., three tablets, each delivering 500 mcg of Semaglutide) preferably provides a total of about 1.5 mg active Semaglutide and 0.9 mg BPC-157 sublingually. As a further example, twenty-eight (28) 275 mg doses of a sublingual Semaglutide composition (i.e., 28 tablets, each delivering 500 mcg of Semaglutide) preferably provides a total of about 14 mg active Semaglutide and 8.4 mg BPC-157 sublingually. In other examples, three (3) 275 mg doses of a high dose sublingual Semaglutide composition (i.e., three tablets, each delivering 750 mcg of Semaglutide) preferably provides a total of about 2.25 mg active Semaglutide and 0.9 mg BPC-157 sublingually. Also, by example, twenty-eight (28) 275 mg doses of a high dose sublingual Semaglutide composition (i.e., 28 tablets, each delivering 750 mcg of Semaglutide) preferably provides a total of about 21 mg active Semaglutide and 8.4 mg BPC-157 sublingually.

Sublingual Semaglutide compositions and methods of use thereof are provided. In the detailed description herein, references to "various embodiments", "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

Benefits, other advantages, and solutions to problems have been described herein with regard to specific embodiments. However, the benefits, advantages, solutions to problems, and any elements that may cause any benefit, advantage, or solution to occur or become more pronounced are not to be construed as critical, required, or essential features or elements of the disclosure. The scope of the disclosure is accordingly to be limited by nothing other than the appended claims, in which reference to an element in the singular is not intended to mean "one and only one" unless explicitly so stated, but rather "one or more." Moreover, where a phrase similar to 'at least one of A, B, and C' or 'at least one of A, B, or C' is used in the claims or specification, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C.

All structural, chemical, and functional equivalents to the elements of the above-described various embodiments that are known to those of ordinary skill in the art are expressly incorporated herein by reference and are intended to be encompassed by the present claims. Moreover, it is not necessary for a composition or method to address each and every problem sought to be solved by the present disclosure, for it to be encompassed by the present claims. Furthermore, no element, component, or method step in the present disclosure is intended to be dedicated to the public regardless of whether the element, component, or method step is explicitly recited in the claims. No claim element is intended to invoke 35 U.S.C. 112(f) unless the element is expressly recited using the phrase "means for." As used herein, the terms "comprises," "comprising," or any other variation thereof, are intended to cover a non-exclusive inclusion, such that a chemical, chemical composition, process, method, article, or apparatus that comprises a list of elements does not include only those elements but may include other elements not expressly listed or inherent to such chemical, chemical composition, process, method, article, or apparatus.

The invention claimed is:

1. A sublingual tablet for sublingual administration consisting essentially of:

0.18 wt. % of Semaglutide sodium;

0.11 wt. % of BPC-157 acetate; and 99.71 wt. % of a carrier comprising untreated fumed silica, sodium stearyl fumarate, microcrystalline cellulose, colloidal silicon dioxide, mannitol, fructose and crospovidone;

wherein the weight percentages are based on the total weight of the tablet.

2. The sublingual tablet of claim 1, wherein each tablet comprises about 500 mcg Semaglutide sodium and about 300 mcg BPC-157 acetate.

3. The sublingual tablet of claim 1, wherein each tablet weighs approximately 275 mg.

4. A sublingual tablet for sublingual administration consisting essentially of:

0.27 wt. % Semaglutide sodium;

0.11 wt. % of BPC-157 acetate; and 99.62 wt. % of a carrier comprising untreated fumed silica, sodium stearyl fumarate, microcrystalline cellulose, colloidal silicon dioxide, mannitol, fructose and crospovidone;

wherein the weight percentages are based on the total weight of the tablet.

5. The sublingual tablet of claim 4, wherein each tablet comprises about 750 mcg Semaglutide sodium and about 300 mcg BPC-157 acetate.

6. The sublingual tablet of claim 4, wherein each tablet weighs approximately 275 mg.

* * * * *